(12) United States Patent
Dakka et al.

(10) Patent No.: US 10,421,699 B2
(45) Date of Patent: Sep. 24, 2019

(54) PRODUCTION OF ISO-OCTENE FROM TERTIARY ALCOHOLS

(71) Applicant: ExxonMobil Research and Engineering Company, Annandale, NJ (US)

(72) Inventors: Jihad M. Dakka, Whitehouse Station, NJ (US); David B. Spry, Lebanon, NJ (US); Cynthia F. Omilian, Whitehouse Station, NJ (US); Matthew S. Ide, Doylestown, PA (US); Jenna L. Walp, Bethlehem, PA (US); Ralph C. Dehaas, Easton, PA (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 0 days.

(21) Appl. No.: 15/839,959

(22) Filed: Dec. 13, 2017

(65) Prior Publication Data

US 2018/0162788 A1 Jun. 14, 2018

Related U.S. Application Data

(60) Provisional application No. 62/433,833, filed on Dec. 14, 2016.

(51) Int. Cl.
*C07C 2/86* (2006.01)
*C07C 2/02* (2006.01)
(Continued)

(52) U.S. Cl.
CPC ........... *C07C 2/864* (2013.01); *B01J 29/7038* (2013.01); *B01J 29/80* (2013.01); *C07C 1/24* (2013.01);
(Continued)

(58) Field of Classification Search
CPC .. C07C 2/86; C07C 2/62; C07C 31/12; C07C 31/125; C07C 29/50
See application file for complete search history.

(56) References Cited

U.S. PATENT DOCUMENTS 3,644,565 A 2/1972 Biale
4,384,161 A 5/1983 Huang
(Continued)

FOREIGN PATENT DOCUMENTS

| EP | 0293032 A1 | 11/1988 |
| EP | 0710622 A1 | 5/1998 |
| WO | 9745383 A1 | 12/1997 |

OTHER PUBLICATIONS

Hajimirzaee (Preparation, modification and characterization of selective zeolite based catalysts for petrochemical applications, Apr. 2015, University of Birmingham) (Year: 2015).*

(Continued)

*Primary Examiner* — Youngsul Jeong
(74) *Attorney, Agent, or Firm* — Andrew T. Ward; Priya G. Prasad

(57) ABSTRACT

Systems and methods are provided for forming alkylate from a tertiary alcohol feed. Olefins for the alkylation reaction can be generated from a portion of the tertiary alcohol feed. The tertiary alcohol feed can be obtained, for example, by selective oxidation to convert a portion of an isoparaffin-containing feed into alcohol, such as conversion of isobutane to t-butyl alcohol. The alcohol can then be converted to an alkene, such as conversion of t-butyl alcohol to isobutene, in the alkylation reaction environment in the presence of a solid acid catalyst. The solid acid catalyst can then facilitate dimerization of the alkenes (e.g. isobutene) to form $C_{8+}$ olefins (e.g. isooctene). A catalyst having an MWW framework is an example of a suitable solid acid catalyst.

23 Claims, 6 Drawing Sheets

(51) Int. Cl.

| | | |
|---|---|---|
| *C07C 1/24* | (2006.01) | |
| *C07C 2/12* | (2006.01) | |
| *C07C 2/62* | (2006.01) | |
| *C07C 31/12* | (2006.01) | |
| *C07C 31/125* | (2006.01) | |
| *C07C 29/50* | (2006.01) | |
| *B01J 29/70* | (2006.01) | |
| *C07C 5/02* | (2006.01) | |
| *C07C 29/132* | (2006.01) | |
| *C07C 5/03* | (2006.01) | |
| *C07C 5/27* | (2006.01) | |
| *C07C 407/00* | (2006.01) | |
| *C10G 45/58* | (2006.01) | |
| *C10G 50/00* | (2006.01) | |
| *C10G 69/12* | (2006.01) | |
| *C10G 3/00* | (2006.01) | |
| *B01J 29/80* | (2006.01) | |
| *B01J 29/50* | (2006.01) | |

(52) U.S. Cl.
CPC ............... *C07C 2/12* (2013.01); *C07C 2/62* (2013.01); *C07C 5/02* (2013.01); *C07C 5/03* (2013.01); *C07C 5/2702* (2013.01); *C07C 29/132* (2013.01); *C07C 29/50* (2013.01); *C07C 31/12* (2013.01); *C07C 31/125* (2013.01); *C07C 407/00* (2013.01); *C10G 3/49* (2013.01); *C10G 45/58* (2013.01); *C10G 50/00* (2013.01); *C10G 69/126* (2013.01); *B01J 29/50* (2013.01); C07C 2523/28 (2013.01); C07C 2523/34 (2013.01); C07C 2523/889 (2013.01); C07C 2529/70 (2013.01); C10G 2300/104 (2013.01); C10G 2300/1044 (2013.01); C10G 2300/1081 (2013.01); C10G 2300/305 (2013.01); C10G 2400/02 (2013.01)

(56) References Cited

U.S. PATENT DOCUMENTS

| | | | |
|---|---|---|---|
| 4,439,409 | A | 3/1984 | Puppe et al. |
| 4,826,667 | A | 5/1989 | Zones et al. |
| 4,954,325 | A | 9/1990 | Rubin et al. |
| 5,236,575 | A | 8/1993 | Bennett et al. |
| 5,243,084 | A | 9/1993 | Cochran et al. |
| 5,250,277 | A | 10/1993 | Kresge et al. |
| 5,254,518 | A | 10/1993 | Soled et al. |
| 5,304,698 | A | 4/1994 | Husain |
| 5,340,562 | A | 8/1994 | O'Young et al. |
| 5,362,697 | A | 11/1994 | Fung et al. |
| 5,382,731 | A | 1/1995 | Chang et al. |
| 5,414,145 | A | 5/1995 | Sheu et al. |
| 5,510,309 | A | 4/1996 | Chang et al. |
| 5,523,509 | A | 6/1996 | O'Young et al. |
| 5,719,097 | A | 2/1998 | Chang et al. |
| 6,077,498 | A | 6/2000 | Diaz et al. |
| 6,231,751 | B1 | 5/2001 | Canos et al. |
| 6,376,731 | B1 | 4/2002 | Evans et al. |
| 6,756,030 | B1 | 6/2004 | Rohde et al. |
| 7,713,513 | B2 | 5/2010 | Jan et al. |
| 7,842,277 | B2 | 11/2010 | Wieslaw et al. |
| 7,982,084 | B1 | 7/2011 | Moscoso et al. |
| 8,704,023 | B2 | 4/2014 | Wieslaw et al. |
| 8,704,025 | B2 | 4/2014 | Wieslaw et al. |
| 2007/0191662 | A1* | 8/2007 | Oikarinen ............... C07C 2/12 585/533 |
| 2014/0243570 | A1* | 8/2014 | Nesterenko ............ B01J 37/10 585/640 |
| 2016/0168048 | A1* | 6/2016 | Wang ..................... C10L 1/04 585/310 |
| 2018/0162786 | A1 | 6/2018 | Dakka et al. |
| 2018/0162787 | A1 | 6/2018 | Dakka et al. |
| 2018/0162788 | A1 | 6/2018 | Dakka et al. |
| 2018/0162789 | A1 | 6/2018 | Liu et al. |

OTHER PUBLICATIONS

Honkela et al. (Thermodynamics and kinetics of the dehydration of tert-butyl alcohol, Ind. Eng. Chem. Res. 2004, 43, pp. 4060-4065 ) (Year: 2004).*

Albright et al., "Alkylation of isobutane with C4 olefins 1. First-step reactions using sulfuric acid catalyst", Ind. Eng. Chem. Res., 1988, vol. 27, pp. 381-386.

Corma et al., "Chemistry, Catalysts, and Processes for Isoparaffin-Olefin Alkylation: Actual Situation and Future Trends", Cat. Rev. Sci. Eng., 1993, vol. 35, pp. 483-570.

Feng et al., "Catalytic decomposition of tert-butyl hydroperoxide into tert-butyl alcohol over Me-OMS-1s molecular sieves", J. Chem. Ind. Eng., 2015, vol. 66, pp. 3965-3970.

Hutson, "Phillips HF Alkylation Process for Alkylation of C3, C4, C5 Olefins", Handbook of Petroleum Refining Processes, R.A. Meyers., Ed.

Lin et al., "Decomposition of tert-butyl hydroperoxide into tert butyl alcohol and O2 catalyzed by bimessite-type manganese oxides: Kinetics and activity", Cat. Comm., 2014, vol. 49, pp. 6-9.

Liu et al., "Catalytic Partial Oxidation of Cyclohexane by Bimetallic Ag/Pd Nanoparticles on Magnesium Oxide", Chem. Eur. J.

Luo et al., "One-pot synthesis of MWW zeolite nanosheets using a rationally designed organic structure-directing agent", Chem. Sci., 2015, vol. 6, pp. 6320-6324.

O'Young, "Hydrothermal Synthesis of Manganese Oxides with Tunnel Structures", in Expanded Clays and Other Microporous Structures, vol. II, 333, M.L. Occelli, H.E. Robson Eds. Van Nostrand Reinhold, NY, 1992.

Shah, "UOP HF Alkylation Process", Handbook of Petroleum Refining Processes, R.A. Meyers, Ed., 1986, pp. XX-XX.

The International Search Report and Written Opinion of PCT/US2017/065954 dated Dec. 13, 2017.

The International Search Report and Written Opinion of PCT/US2017/065955 dated Dec. 13, 2017.

The International Search Report and Written Opinion of PCT/US2017/065958 dated Dec. 13, 2017.

The International Search Report and Written Opinion of PCT/US2017/065960 dated Dec. 13, 2017.

* cited by examiner

PRODUCTION OF ISO-OCTENE FROM TERTIARY ALCOHOLS

CROSS-REFERENCE TO RELATED APPLICATIONS

This application claims the benefit of provisional U.S. Ser. No. 62/433,833, filed Dec. 14, 2016, the entire contents of which are expressly incorporated by reference herein. This application is also related to several other co-pending U.S. applications, filed on even date herewith and bearing U.S. patent application Ser. Nos. 15/839,937 and 15/839,974.

FIELD

Methods are provided for production of iso-octene from tertiary alcohols.

BACKGROUND

In conventional petroleum processes, alkylate is typically used to describe a product formed by an alkaylation process involving an isoparaffin-containing feed and an olefin-containing feed. Industrially, alkylation reactions often correspond to the reaction of a $C_2$ to $C_5$ olefin, normally 2-butene, with isobutane in the presence of an acidic catalyst to produce a so-called alkylate. This alkylate is a valuable blending component in the manufacture of gasoline due not only to its high octane rating but also to its sensitivity to octane-enhancing additives. Industrial isoparaffin-olefin alkylation processes have historically used hydrofluoric or sulfuric acid catalysts under relatively low temperature conditions. The sulfuric acid alkylation reaction is particularly sensitive to temperature, with low temperatures being favored to minimize the side reaction of olefin polymerization. Acid strength in these liquid acid catalyzed alkylation processes is typically maintained at 88 to 94 weight percent by the continuous addition of fresh acid and the continuous withdrawal of spent acid. The hydrofluoric acid process is less temperature sensitive and the acid is more easily recovered and purified. A general discussion of sulfuric acid alkylation can be found in a series of three articles by L. F. Albright et al., "Alkylation of Isobutane with $C_4$ Olefins", 27 Ind. Eng. Chem. Res., 381-397, (1988). For a survey of hydrofluoric acid catalyzed alkylation, see 1 Handbook of Petroleum Refining Processes 23-28 (R. A. Meyers, ed., 1986). An overview of the entire technology can be found in "Chemistry, Catalysts and Processes of Isoparaffin-Olefin Alkylation—Actual Situation and Future Trends, Corma et al., Catal. Rev. Sci. Eng. 35(4), 483-570 (1993).

Both sulfuric acid and hydrofluoric acid alkylation share inherent drawbacks including environmental and safety concerns, acid consumption, and sludge disposal. Research efforts have, therefore, been directed to developing alkylation catalysts which are equally as effective as, or more effective than, sulfuric or hydrofluoric acids but which avoid many of the problems associated with these two acids.

U.S. Pat. No. 3,644,565 discloses alkylation of a paraffin with an olefin in the presence of a catalyst comprising a Group VIII noble metal present on a crystalline aluminosilicate zeolite having pores of substantially uniform diameter from about 4 to 18 angstrom units and a silica to alumina ratio of 2.5 to 10, such as zeolite Y. The catalyst is pretreated with hydrogen to promote selectivity.

U.S. Pat. No. 4,384,161 describes a process of alkylating isoparaffins with olefins to provide alkylate using a large-pore zeolite catalyst capable of absorbing 2,2,4-trimethylpentane, for example, ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The addition of a Lewis acid is reported to increase the activity and selectivity of the zeolite, thereby effecting alkylation with high olefin space velocity and low isoparaffin/olefin ratio.

U.S. Pat. No. 5,304,698 describes a process for the catalytic alkylation of an olefin with an isoparaffin comprising contacting an olefin-containing feed with an isoparaffin-containing feed with a crystalline microporous material selected from the group consisting of MCM-22, MCM-36, and MCM-49 under alkylation conversion conditions of temperature at least equal to the critical temperature of the principal isoparaffin component of the feed and pressure at least equal to the critical pressure of the principal isoparaffin component of the feed.

An additional difficulty with alkylation processes can be related to the availability and/or cost of the feeds for forming alkylate. Light paraffin feeds, such as a feed containing isobutane, are generally considered low cost feeds. However, the corresponding olefin feed for forming alkylate can generally be of higher cost, particularly when the corresponding olefin feed corresponds to a $C_{3+}$ olefin feed, such as a feed of butene or isobutene, because these olefins are typically produced via dehydrogenation reaction which is a high temperature, thermodynamically limited process.

U.S. Pat. No. 5,243,084 describes a process for oxidation of isobutane to tertiary butyl hydroperoxide and tertiary butyl alcohol.

U.S. Patent Application No. 62/433,833 filed on Dec. 14, 2016 describes a process of selectively oxidizing an isoparaffin feed to an alcohol, such as isobutane to t-butyl alcohol, and then converting the alcohol to an alkene. A solid acid catalyst can facilitate conversion of tertiary alcohols to alkene under alkylation conditions. The solid acid catalyst can then facilitate alkylation of isoparaffin using the in-situ formed alkenes in the presence of the in-situ formed water.

SUMMARY

Provided herein are methods for the production of iso-octene. In general, the methods comprise exposing a tert-butyl alcohol ("TBA") containing feed to a solid acid catalyst, wherein the solid acid catalyst comprises a crystalline microporous material of the MWW framework type, under dehydration conditions to convert a percentage of TBA to isobutene to form an isobutene containing feed; exposing at least a portion of the isobutene containing feed to a second solid acid catalyst, wherein the second solid acid catalyst comprises a crystalline microporous material of the MWW framework type, under dimerization conditions to dimerize isobutene molecules in the isobutene containing feed to iso-octene to form an iso-octene containing feed; wherein greater than 50% of the iso-octene molecules in the iso-octene containing feed comprise trimethylpentene relative to weight of the iso-octene feed. In another aspect, the iso-octene feed can by hydrogenated to form an iso-octane containing feed, the iso-octane containing feed potentially having an octane rating, as determined by (RON+MON)/2, of at least 95, e.g. at least 98 or at least 100.

In certain aspects, the crystalline microporous material of the MWW framework type of either the first or second solid acid catalyst is selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and mixtures thereof. In other aspects, the solid acid catalyst(s) may comprise a mixed metal oxide based on oxides of Fe/W/Zr, W/Zr, Ce/W/Zr, Cu/W/Zr, Mn/W/Zr, or a combination thereof. In yet another aspect, the solid acid catalyst(s) may further comprise an inorganic oxide binder. The solid acid catalyst and the second solid acid catalyst may be the same or different and may be located in the same or different reactor vessel(s).

The processes described herein are quite selective for target molecules. For example, in certain aspects, greater than 90%, e.g. greater than 95%, of the iso-octene molecules in the iso-octene containing feed comprise trimethylpentene. Additionally or alternatively, the trimethylpentene comprises 2,4,4,-trimethyl-1-pentene and 2,4,4,-trimethyl-2-pentene, wherein the ratio of 2,4,4,-trimethyl-1-pentene to 2,4,4,-trimethyl-2-pentene is greater than about 2, e.g. about 2 to about 4.

The TBA containing feed may produced by any convenient means. In certain aspects the TBA containing feed is produced by oxidizing isobutane. The TBA containing feed may also be co-fed with an isobutane feed, or other $C_{4+}$ paraffins. Additionally or alternatively, the isobutane feed co-fed with the TBA containing feed may be oxidized upstream of the process to produce the TBA containing feed. In yet another aspect, the TBA containing feed may also include one or more oxygenates, the one or more oxygenates comprising water, methanol, acetone, or a combination thereof, e.g. methanol and acetone, or water methanol and acetone, or water. In certain aspects, it may be advantageous to add water to the TBA containing feed beyond that which is produced during the dehydration of TBA to form isobutene. In other circumstances, it may be advantageous to separate out methanol and/or acetone from the TBA containing feed and utilize those components in other known refinery applications.

In another aspect dimerization conditions can include a dimerization temperature of about 100° C. to about 210° C., e.g. about 150° C. to about 190° C., and a dimerization pressure of about 15 psig to about 1000 psig. In yet another aspect, the $C_8$ hydrocarbon portion of the dimerization effluent has an octane rating, as determined by (RON+MON)/2, of at least 95, e.g. at least 98 or at least 100.

Additionally, a person of skill in the art would understand that the steps of oxidizing of isobutane to form TBA and then subsequent dehydration of TBA to form isobutene and water may be omitted in favor of providing an isobutene feed and adding water to achieve similar results to what is disclosed herein.

DETAILED DESCRIPTION

Overview

In various aspects, systems and methods are provided for forming alkylate from an tertiary alcohol, such as tert-butyl alcohol (TBA), containing feed. Instead of using an olefin co-feed to form alkylate or an isoparaffin-containing feed, olefins for the alkylation reaction can be generated from a portion of the TBA-containing feed. This can be achieved, for example, by converting the tertiary alcohol to an alkene, such as conversion of t-butyl alcohol to isobutene, in the alkylation reaction environment. It has been unexpectedly discovered that a solid acid catalyst can facilitate conversion of tertiary alcohols to alkene under alkylation conditions. A solid acid catalyst can then facilitate dimerization of the in-situ formed isobutene in the presence of the in-situ formed water to isooctene. The isooctene can then easily be hydrogenated to isooctane. This conversion of alcohol to alkene, and then alkene dimerization, can occur in part due to the ability of a solid acid catalyst to tolerate water. Moreover and surprisingly, the presence of water combined with the appropriate reaction temperature promotes dimerization of the alkene, but suppresses further polymerizations. A catalyst having an MWW framework is an example of a suitable solid acid catalyst.

Figure 1:
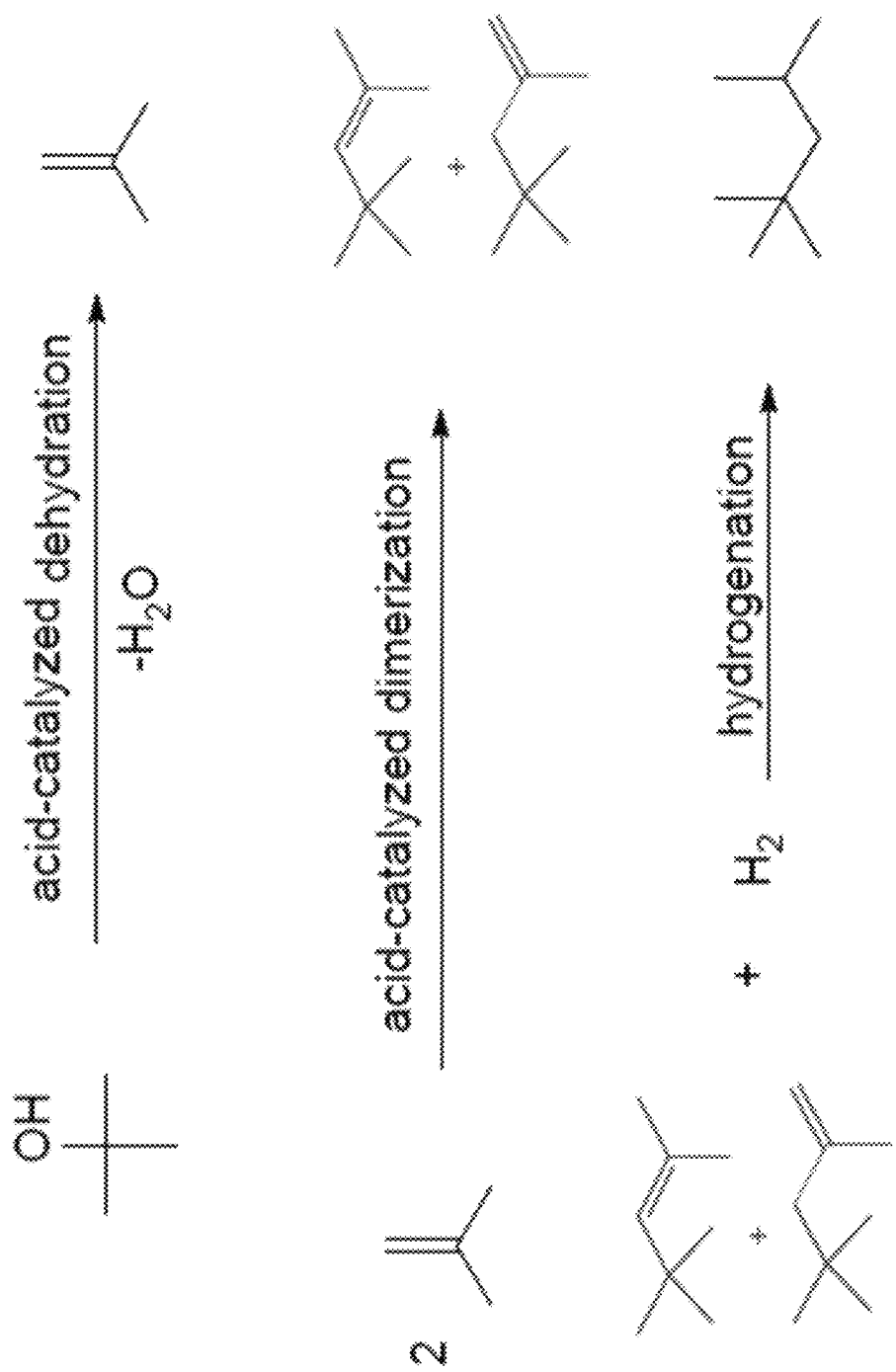
FIG. 1 show an example of a reaction scheme for forming alkylate from tertiary alcohols via dehydration and subsequent dimerization.

FIG. 1 shows an example of the overall reaction scheme that can be used to form alkylate from a tertiary alcohol feed. In a first reactor and/or reaction stage, a tertiary alcohol feed (or a portion of such a feed) can be exposed to acid-catalyzed dehydration conditions. In FIG. 1, the tertiary alcohol feed is represented by TBA. TBA can oftentimes be formed through oxidation of an isoparaffin feed, such as iso-butane. This method of forming TBA results in various additional side products, such as methanol, water and acetone. This mixture of TBA and some oxygenates has been found to be an effective feed, without separation, in the presently described process. The acid-catalyzed dehydration conditions can result in substantial conversion of the feed, so that the resulting products include a substantial portion of isobutene. In a second reactor and/or reaction stage, the isobutene (and optionally at least a portion of the additional side products) can be exposed to a solid acid catalyst under controlled dimerization conditions. Under the appropriate conditions using suitable solid acid catalysts, the isobutene is dimerized, but not further polymerized, to form isooctene. Moreover, under the appropriate dimerization conditions the dimerization reaction is overwhelmingly selective for trimethylpentene over dimethylhexene. Additionally, the trimethylpentene product has a greater proportion 2,4,4,-trimethyl-1-pentene to 2,4,4,-trimethyl-2-pentene. This is significant because trimethylpentene has a higher octane rating than dimethylhexene and 2,4,4,-trimethyl-1-pentene is preferable to 2,4,4-trimethyl-2-pentene because terminal olefins are generally more active towards hydrogenation than internal olefins due to steric hindrance.

Some examples of solid acid catalysts include zeolitic catalysts, such as catalysts having an MWW framework type. An MWW framework catalyst corresponds to a catalyst including a crystalline microporous material of the MWW framework type. The solid acid catalyst can convert the TBA to isobutene at substantially 100% conversion, and then dimerize the isobutene, resulting in the formation of isooctene, such as the 2,4,4-trimethylpentene. This isooctene can then be hydrogenated to form isooctane, such as 2,4,4-trimethylpentane. The full reaction scheme described above is shown in FIG. 1. The net result can be the upgrading of a low value tertiary alcohol stream to high octane blending component for gasoline.

A common method for characterizing the octane rating of a composition is to use an average of the Research Octane Number (RON) and the Motor Octane Number (MON) for a composition. This type of octane rating can be used to determine the likelihood of "knocking" behavior when operating a conventional spark ignition engine. In this discussion, octane rating is defined as (RON+MON)/2, where RON is research octane number and MON is motor octane number. Although various methods are available for determining RON and MON, in the claims below, references to Research Octane Number (RON) correspond to RON determined according to ASTM D2699, while references to Motor Octane Number (MON) correspond to MON determined according to ASTM D2700.

In this discussion, the naphtha boiling range is defined as about 50° F. (~10° C., roughly corresponding to the lowest boiling point of a pentane isomer) to 350° F. (~177° C.). It is noted that due to practical consideration during fractionation (or other boiling point based separation) of hydrocarbon-like fractions, a fuel fraction formed according to the methods described herein may have a T5 or a T95 distillation point corresponding to the above values, as opposed to having initial/final boiling points corresponding to the above values. Compounds ($C_{4-}$) with a boiling point below the naphtha boiling range can be referred to as light ends. Optionally, a naphtha boiling range fuel composition can have a higher T5 distillation point, such as a T5 distillation point of at least about 15° C., or at least about 20° C., or at least about 30° C. In particular, a naphtha boiling range fuel composition can have a T5 to T95 distillation point range corresponding to a T5 of at least about 10° C. and a T95 of about 177° C. or less; or a T5 of at least about 15° C. and a T95 of about 177° C. or less. In the claims below, ASTM D86 should be used for determining boiling points (including fractional weight boiling points). Compounds with boiling points above 177° C. can correspond to distillate fuel boiling range compounds.

Solid acid catalysts can generally refer to solid materials that can provide acidic sites for catalysis of reactions. Some examples of solid acid catalysts can include various types of zeolites and/or molecular sieves. For example, in zeolitic structures that include silicon and aluminum in the framework, the aluminum atoms can potentially serve as acidic catalysis sites. Suitable zeolitic materials for use as solid acid catalysts can include ZSM-4, ZSM-20, ZSM-3, ZSM-18, zeolite Beta, faujasite, mordenite, zeolite Y and the rare earth metal-containing forms thereof. More generally, crystalline materials having a porous framework structure built from tetrahedra atoms connected by bridging oxygen atoms can potentially be suitable solid acid catalysts. This can include aluminosilicates having a zeolitic framework as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework. Still other examples of solid acid catalysts can include mixed metal oxides. Examples of suitable mixed metal oxides can include mixed metal oxides based on oxides of Fe/W/Zr, W/Zr, Ce/W/Zr, Cu/W/Zr, and/or Mn/W/Zr.

As used herein, the term "crystalline microporous material of the MWW framework type" includes one or more of: a) Molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, which is incorporated by reference with respect to definitions for unit cells, building blocks, and crystal structures); b) Molecular sieves made from a common second degree building block, being a 2-dimensional tiling of such MWW framework topology unit cells, forming a monolayer of one unit cell thickness, preferably one c-unit cell thickness; c) Molecular sieves made from common second degree building blocks, being layers of one or more than one unit cell thickness, wherein the layer of more than one unit cell thickness is made from stacking, packing, or binding at least two monolayers of MWW framework topology unit cells. The stacking of such second degree building blocks can be in a regular fashion, an irregular fashion, a random fashion, or any combination thereof; and d) molecular sieves made by any regular or random 2-dimensional or 3-dimensional combination of unit cells having the MWW framework topology.

Crystalline microporous materials of the MWW framework type include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Examples of crystalline microporous materials of the MWW framework type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), UZM-8HS (described in U.S. Pat. No. 7,713,513), UZM-37 (described in U.S. Pat. No. 7,982,084); EMM-10 (described in U.S. Pat. No. 7,842,277), EMM-12 (described in U.S. Pat. No. 8,704,025), EMM-13 (described in U.S. Pat. No. 8,704,023), MIT-1 (described by Luo et al in Chem. Sci., 2015, 6, 6320-6324), and mixtures thereof, with MCM-49 generally being preferred.

In some embodiments, the crystalline microporous material of the MWW framework type employed herein may be an aluminosilicate material having a silica to alumina molar ratio of at least 10, such as at least 10 to less than 50.

In some embodiments, the crystalline microporous material of the MWW framework type employed herein may be contaminated with other crystalline materials, such as ferrierite or quartz. These contaminants may be present in quantities of less than about 10% by weight, normally less than about 5% by weight.

The above molecular sieves may be formed into extrudates with or without another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia, or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide binder may vary widely. For example, the amount of binder employed may be as little as 0 wt %, or alternatively at least 1 wt %, or at least 5 wt %, or at least 10 wt %, whereas in other embodiments the catalyst may include up to 90 wt %, for example up 80 wt %, such as up to 70 wt %, for example up to 60 wt %, such as up to 50 wt % of a binder material.

In an aspect, a solid acid catalyst can be substantially free of any binder containing amorphous alumina. As used herein, the term "substantially free of any binder containing amorphous alumina" means that the solid acid catalyst used herein contains less than 5 wt %, such as less than 1 wt %, and preferably no measurable amount, of amorphous alumina as a binder. Surprisingly, it is found that when the solid acid catalyst is substantially free of any binder containing amorphous alumina, the activity of the catalyst for isoparaffin-olefin alkylation can be significantly increased, for example by at least 50%, such as at least 75%, even at least 100% as compared with the activity of an identical catalyst but with an amorphous alumina binder.

Production of TBA Through Oxidation of Isobutane

Oxidation of isobutane for formation of t-butyl hydroperoxide is a known industrial process. While this oxidation process is often employed for production of peroxides, the process also generates t-butyl alcohol. The amount of alcohol production can vary depending on the conditions and the reaction configuration. For example, U.S. Pat. No. 5,243,084 describes systems and methods for producing t-butyl alcohol as a product from oxidation of isobutane.

In various aspects, oxidation of isobutane (and/or other $C_5$-$C_6$ isoparaffins) to form t-butyl alcohol (and/or other tertiary $C_5$-$C_6$ alcohols) can be performed by any convenient known oxidation method. The isoparaffin-containing feed can correspond to a feed including isobutane, $C_{4+}$ isoparaffins, $C_{5+}$ isoparaffins, $C_4$-$C_5$ isoparaffins, or $C_4$-$C_6$ isoparaffins. In some aspects, the isoparaffin-containing feed can contain at least 80 wt % of isoparaffins (and up to 100 wt %), or at least 90 wt %, or at least 95 wt %, or at least 99 wt %, such as a feed that substantially contains isoparaffins (i.e., 99.5 wt % or higher). In some aspects, the isoparaffin-containing feed can correspond to an isobutane-containing feed that contains at least 80 wt % of isobutane (and up to 100 wt %), or at least 90 wt %, or at least 95 wt %, or at least 99 wt %, such as a feed that substantially contains isobutane (i.e., 99.5 wt % or higher). In various aspects, other components present in the isoparaffin-containing feed (such as an isobutane-containing feed) can include n-paraffins, cycloparaffins, and/or less than about 2 wt % of compounds typically present due to the nature of a process that generated the isoparaffin feed.

As an example, isobutane can be reacted with oxygen in a reactor to produce a mixture of t-butyl hydroperoxide along with t-butyl alcohol. The isobutane oxidation reaction conditions in the oxidation reactor can include, for example, a reaction temperature of about 100° C. to about 200° C., a pressure of about 200 psig (~1.4 MPag) to about 500 psig (~3.4 MPag), and a residence time in the oxidation zone of about 1 hour to about 15 hours. Oxygen can be used as the oxidant, although minor amounts of nitrogen and/or other inert gases can also be present.

The above reaction conditions can generate a weight ratio of t-butyl alcohol to t-butyl hydroperoxide in the liquid phase of about 0.8. Due to the higher vapor pressure of t-butyl alcohol, withdrawing the vapor above the reaction zone can result in a gas phase product with a weight ratio of t-butyl alcohol to t-butyl hydroperoxide of roughly 1.0. This can be facilitated, for example, by operating the oxidation reactor to maintain the reaction mixture at or near the boiling point. The withdrawn vapor can also include, for example, unreacted isobutane and other additional reaction side products. These additional reaction products can include, for example, water and oxygenate impurities, such as methanol and acetone. Depending on the nature of the fractionation, the ratio of t-butyl alcohol to t-butyl hydroperoxide can be further increased. In some aspects, a fraction enriched in t-butyl hydroperoxide can be returned to the oxidation reactor. For a fraction containing t-butyl alcohol, the fraction can optionally be exposed to elevated temperatures of about 100° C. to about 200° C. for additional time to allow for further decomposition of t-butyl hydroperoxide to t-butyl alcohol. Without being bound by any particular theory, it is believed that forming alcohols from isoparaffins by oxidation as described herein can provide a method for alcohol formation under lower severity conditions in comparison with processes such as high temperature reforming. This can allow the conditions for formation of alcohol to be more similar to the eventual conditions for alkylate formation. Additionally or alternately, it is believed that the selectivity of alcohol formation can be improved relative to a high temperature reforming process.

It is noted that other isoparaffins can potentially be oxidized to generate tertiary alcohols. For example, an isopentane or isohexane feed could be oxidized to generated tertiary alcohols. This could be useful, for example, if an available source of isoparaffins includes a mixture of $C_{4+}$ isoparaffins. While use of higher carbon number isoparaffins could lead to formation of compounds during alkylation that are above the traditional naphtha boiling range for gasoline formation, such heavier compounds can be readily separated by boiling point separation and used as part of a distillate fuel fraction.

Another potential difficulty with $C_{5+}$ isoparaffins is that such isoparaffins contain multiple types of carbon sites. Isobutane corresponds to an isoparaffin with three primary (i.e., terminal) carbons and one tertiary carbon. When isobutane is oxidized, the selectivity for forming t-butyl alcohol is high, as the primary carbons have only a limited ability to stabilize the reaction intermediates that could allow for formation of an alcohol. Additionally, once t-butyl alcohol is formed, little or no transfer of the alcohol from the tertiary carbon to a primary carbon would be expected. By contrast, an isopentane (such as 2-methylbutane) includes 3 primary carbons, a tertiary carbon, and a secondary carbon. While the tertiary carbon is the most favorable location for formation of an alcohol, the secondary carbon can also be a suitable location. As a result, oxidation of a $C_{5+}$ isoparaffin can typically result in formation of a mixture of alcohols. Additionally, the presence of multiple non-primary carbons can also facilitate migration of the alcohol group after formation and/or migration of the double bond in the resulting in-situ olefin. As a result, using alcohols formed from $C_{5+}$ paraffins can tend to lead to production of a larger mixture of alkylate products, as opposed to the relatively high selectivity for formation of tri-methylpentanes that is exhibited when isobutane is used as the feed for oxidation. Because tri-methylpentanes can have a relatively high octane value, the formation of a wider variety of products when using $C_{5+}$ isoparaffins can tend to reduce the octane value of the resulting alkylate.

Formation of Isooctene from t-Butyl Alcohol

In various aspects, a feed of t-butyl alcohol or a mixed feed of isobutane and t-butyl alcohol can be formed based on generation of t-butyl alcohol as described above. In some aspects, the feed can include isobutane and t-butyl alcohol in a molar ratio and/or volume ratio of about 1:1 to about 40:1. In another aspect, the feed does not include any isobutane. Optionally, the feed can also include other oxygenates, such as methanol and/or acetone formed as additional products during oxidation. More generally, the molar ratio and/or volume ratio of isoparaffin to tertiary alcohol in the reactor feed can be from about 2:1 to about 100:1, or about 10:1 to about 75:1, or about 10:1 to about 40:1. Optionally, one or more additional oxygenate products generated during oxidation, such as methanol and/or acetone, may be included as part of the oxidation product fraction containing the t-butyl alcohol. In some aspects, the molar ratio and/or volume ratio of t-butyl alcohol to acetone in an oxidation product fraction (and/or the feed to alkylation) can be about 8:1 to about 200:1, or about 8:1 to about 100:1, or about 10:1 to about 150:1. In some aspects, the molar ratio and/or volume ratio of t-butyl alcohol to methanol in an oxidation product fraction (and/or the feed to alkylation) can be about 8:1 to about 200:1, or about 8:1 to about 100:1, or about 10:1 to about 150:1. At typical alkylation temperatures, the volume ratio of components in an alkylation feed and/or in an alkylation effluent can be similar to the molar ratio.

During the process, the t-butyl alcohol (and/or other tertiary alcohol) can be substantially quantitatively converted to olefin and water under the dehydration conditions in the presence of a solid acid catalyst. The resulting isobutene olefins can then dimerize to form isooctene under dimerization conditions in the presence of the solid acid catalyst. In an alternative embodiment of the process, one may start with isobutane and simply add water to mimic the dehydration of t-butyl alcohol reaction products.

Operating pressure can suitably be from about 15 to about 1500 psig (~104 kPag to ~10.3 MPag), such as about 400 psig (~2.8 MPag) to about 1000 psig (6.9 MPag). In some aspects, the operating temperature can be from about 100° C. to about 210° C., or about 130° C. to about 190° C., or about 150° C. to about 170° C. Without being bound to a particular theory, it is believed that the presence of water in the feed, or the alcohol that dehydrates to form water and an olefin, selectively adsorbs on strong acid sites (often Bronsted acid sites) found in microporous zeolite catalysts. The adsorption of the water on the acid site decreases the acid strength of the acid site, which in turn significantly decreases the capability of the catalyst to enable further polymerizations that require these strong acid sites. The low operating temperature is required because the concentration of water adsorbed on the acid sites is a direct function of temperature. High temperature will cause water to desorb from the acid site opening up the pathway for subsequent olefin dimerization reactions—i.e. formation of hydrocarbons greater than the desired $C_8$ olefins—while lower temperature will decrease this reaction.

Hydrocarbon flow through the alkylation reaction zone containing the catalyst is typically controlled to provide an olefin liquid hourly space velocity (LHSV) sufficient to convert about 99 percent by weight of the fresh olefin to alkylate product. In some embodiments, olefin LHSV values fall within the range of about 0.01 to about 10 $hr^{-1}$. Because the conversion of tertiary alcohol to olefin in the reactor is substantially quantitative, the olefin LHSV and the tertiary alcohol LHSV can be roughly the same.

The product composition of the olefin dimerization reaction described herein can be dependent on the reaction conditions. As will be shown in the examples, however, under the appropriate temperature, pressure, and solid acid catalyst, conversion of TBA to isobutene and subsequent conversion of isobutene to isooctene can be achieved at very high percentages. Moreover, the isooctene formed is highly selective for trimethylpentene over dimethylhexene. Additionally, of the trimethylpentene formed, a large proportion is 2,4,4-trimethyl-1-pentene as compared to 2,4,4-trimethyl-2-pentene. This is significant because trimethylpentene has a higher octane rating than dimethyhexene and 2,4,4-trimethyl-1-pentene is preferable to 2,4,4-trimethyl-2-pentene because terminal olefins are generally more active towards hydrogenation than internal olefins due to steric hindrance. The isooctene product can then be hydrogenated to form isooctane. As discussed, this can correspond to an alkylate product having a higher octane value than would be obtained by a comparable process where isobutane and isobutene feeds are reacted using sulfuric acid as the catalyst. In some aspects, a naphtha boiling range portion of the alkylation effluent can have an octane rating, as determined based on (RON+MON)/2, of at least 95, of at least 98, or at least 100. In particular, in some aspects the naphtha boiling range portion of the alkylation effluent can have an octane rating of about 95 to about 100, or about 98 to about 102. Additionally, in aspects where oxygenate impurities are present in the initial feed to the alkylation reaction, a portion of those impurities can be present in the alkylation effluent. For example, acetone generated during selective oxidation of isobutane may not be fully converted under alkylation conditions. In aspects where acetone from a selective oxidation process is included as part of the feed to the alkylation reactor, unconverted acetone can correspond to 0.01 mol % to 0.5 mol % of the alkylation effluent on a dry basis, or 0.05 mol % to 0.5 mol %. Dry basis refers to the hydrocarbon portion of the alkylation effluent, which excludes any water present in the alkylation effluent.

Example 1

Preparation of 80 wt % MCM-49/20 wt % Alumina Catalyst 80 parts MCM-49 zeolite crystals were combined with 20 parts pseudoboehmite alumina, on a calcined dry weight basis. The MCM-49 and pseudoboehmite alumina dry powder were placed in a muller or a mixer and mixed for about 10 to 30 minutes. Sufficient water and 0.05% polyvinyl alcohol were added to the MCM-49 and alumina during the mixing process to produce an extrudable paste. The extrudable paste was formed into a ½ inch quadralobe extrudate using an extruder. After extrusion, the 1/20th inch quadralobe extrudate was dried at a temperature ranging from 250° F. to 325° F. (121° C. to 163° C.). After drying, the dried extrudate was heated to 1000° F. (538° C.) under flowing nitrogen. The extrudate was then cooled to ambient temperature and humidified with saturated air or steam.

After humidification, the extrudate was ion exchanged with 0.5 to 1 N ammonium nitrate solution. The ammonium nitrate solution ion exchange was repeated. The ammonium nitrate exchanged extrudate was then washed with deionized water to remove residual nitrate prior to calcination in air. After washing the wet extrudate was dried. The exchanged and dried extrudate was then calcined in a nitrogen/air mixture to a temperature 1000° F. (538° C.).

Example 2

Preparation of ZSM-48 Catalyst (Comparative)

ZSM-48 zeolite crystals were combined with 35 parts pseudoboehmite alumina, on a calcined dry weight basis. The ZSM-48 and pseudoboehmite alumina dry powder were placed in a muller or a mixer and mixed for about 10 to 30 minutes. Sufficient water was added to the ZSM-48 and alumina during the mixing process to produce an extrudable paste. The extrudable paste was formed into a 1/16th inch quadralobe extrudate using an extruder. After extrusion, the 1/16th inch quadralobe extrudate was dried at a temperature ranging from 250° F. to 325° F. (168° C.). After drying, the dried extrudate was heated to 1000° F. (538° C.) under flowing nitrogen. The extrudate was then cooled to ambient temperature and humidified with saturated air or steam.

After the humidification, the extrudate was ion exchanged with 0.5 to 1 N ammonium nitrate solution. The ammonium nitrate solution ion exchange was repeated. The ammonium nitrate exchanged extrudate was then washed with deionized water to remove residual nitrate prior to calcination in air. After washing the wet extrudate was dried. The exchanged and dried extrudate was then calcined in a nitrogen/air mixture to 1000° F. (538° C.). Following calcination, the extrudate was steamed at 700° F. (371° C.) for 3 hours.

Example 3

Procedure for Dehydration/Dimerization

For dehydration/dimerization, a single reactor fixed bed isothermal pilot plant was operated without product recycle. The reactor used in these experiments comprised a stainless steel tube having an internal diameter of ⅜ inches (~0.95 cm), a length of 20.5 inches (~52 cm) and a wall thickness of 0.035 inches (~0.089 cm). A piece of stainless steel tubing 8¾ inches (~22.2 cm) long×⅜ inches (~0.95 cm) external diameter and a piece of ¼ inch (~0.64 cm) tubing of similar length were positioned in the bottom of the reactor (one inside of the other) as a spacer to position and support the catalyst in the isothermal zone of the furnace. A ¼ inch (~0.64 cm) plug of glass wool was placed at the top of the spacer to keep the catalyst in place. A ⅛ inch (~0.32 cm) stainless steel thermo-well was placed in the catalyst bed, long enough to monitor temperature throughout the catalyst bed using a movable thermocouple. The catalyst was loaded with a spacer at the bottom to keep the catalyst bed in the center of the furnace's isothermal zone.

The catalyst was then loaded into the reactor from the top. The catalyst bed contained about 4.0 g of the MCM-49 catalyst of Example 1 or 4.0 g of the ZSM-48 catalyst of Example 2 sized to 14-25 mesh (700 to 1400 micron) and was 10 cm in length. A ¼ inch (~0.32 cm) plug of glass wool was placed at the top of the catalyst bed to separate quartz chips from the catalyst. The remaining void space at the top of the reactor was filled with quartz chips of similar size to the catalyst or larger (such as up to 14 mesh). The reactor was installed in the furnace with the catalyst bed in the middle of the furnace at the pre-marked isothermal zone. The reactor was then pressure and leak tested at 800 psig (~5.5 MPag).

500 cc ISCO syringe pumps were used to introduce the feed to the reactor. One ISCO pump was used for pumping an isobutene feed and a second ISCO pump was used to pump a blend of TBA (88 wt %), acetone (8 wt %), and methanol (4 wt %), hereinafter referred to as the TBA Blend. A Grove "Mity Mite" back pressure controller was used to control the reactor pressure, typically set at about 350 psig (~2.4 MPag) or about 750 psig (~5.2 MPag). On-line GC analyses were taken to verify feed and the product composition. The feed (chemical grade isobutane and the TBA Blend were used) was then pumped through the catalyst bed with the catalyst bed held at 150° C., 170° C., and 190° C. at different times during the experiments. The products exiting the reactor flowed through heated lines routed to GC then to cold (5-7° C.) collection pots in series. The non-condensable gas products were routed through a gas pump for analyzing the gas effluent. Material balances were taken at 24 hr intervals. Samples were taken for analysis. The material balance and the gas samples were taken at the same time while an on-line GC analysis was conducted for doing material balance.

Example 4

Dehydration/Dimerization of TBA in the Presence and Absence of Isobutane Over MCM 49

The catalyst described in Example 1 (MCM-49 of the MWW framework type) was tested in the unit with two different feeds using the procedure outlined in Example 3. The first feed was a 3:1 by volume mixture of isobutene and the TBA Blend. The second feed was the TBA Blend alone, without isobutene. The reaction was conducted with varying temperature, pressure, and space velocity (LHSV). The reaction conditions are summarized in Table 1 below.

TABLE 1

| T.O.S Hr | feed | LHSV | Press, PSIG | Temp ° C. |
|---|---|---|---|---|
| 0-108 | 15 CC iso-butane, 5 cc blend (88% TBA, 8% acetone, 4% MeOH) | 2 | 750 | 150 |

TABLE 1-continued

| T.O.S Hr | feed | LHSV | Press, PSIG | Temp ° C. |
|---|---|---|---|---|
| 120-420 | 15 CC iso-butane, 5 cc blend (88% TBA, 8% acetone, 4% MeOH) | 2 | 750 | 170 |
| 432-504 | 15 CC iso-butane, 5 cc blend (88% TBA, 8% acetone, 4% MeOH) | 2 | 750 | 190 |
| 516-564 | 15 CC iso-butane, 5 cc blend (88% TBA, 8% acetone, 4% MeOH) | 2 | 350 | 190 |
| 576-732 | 15 CC iso-butane, 5 cc blend (88% TBA, 8% acetone, 4% MeOH) | 2 | 350 | 170 |
| 744-888 | 15 CC iso-butane, 5 cc blend (88% TBA, 8% acetone, 4% MeOH) | 1 | 350 | 170 |
| 900-1020 | 15 CC iso-butane, 5 cc blend (88% TBA, 8% acetone, 4% MeOH) | 2 | 750 | 170 |
| 1032-1200 | 15 CC iso-butane, 5 cc blend (88% TBA, 8% acetone, 4% MeOH) | 1 | 750 | 170 |
| 1212-1332 | 15 CC iso-butane, 5 cc blend (88% TBA, 8% acetone, 4% MeOH) | 0.5 | 750 | 170 |
| 1344-1572 | 5 cc blend (88% TBA, 8% acetone, 4% MeOH) | 0.5 | 750 | 170 |
| 1596-1788 | 15 CC iso-butane, 5 cc blend (88% TBA, 8% acetone, 4% MeOH) | 2 | 750 | 170 |
| 1812-1980 | 5 cc blend (88% TBA, 8% acetone, 4% MeOH) | 0.5 | 750 | 190 |

Figure 2:
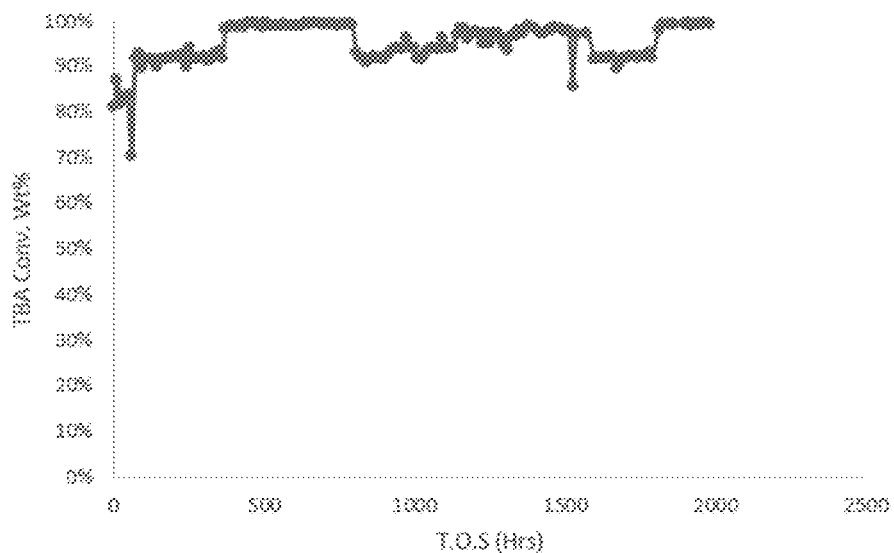
FIG. 2 depicts conversion rate of TBA under various conversion conditions described in Example 4.

As can be seen from FIG. 2, TBA conversion is greater than 90% for the majority of the time on stream under the various process conditions. Nearly 100% conversion is achieved from about 400 hours to about 800 hours, from about 1200 hours to about 1600 hours, and from about 1800 hours to about 2000 hours. This high conversion rate is achieved seemingly irrespective of whether iso-butane is co-fed with the TBA or not. It is believed that substantially all of the converted TBA results in formation of isobutene. Based on the results shown in FIG. 2, it appears that MWW framework catalysts such as MCM-49 are suitable for substantially complete in-situ conversion of TBA to isobutene under alkylation reaction conditions. More generally, solid acid catalysts (such as MWW framework catalysts) are believed to be suitable for conversion of TBA into isobutene, as well as potentially suitable for conversion of other tertiary alcohols to iso-olefins.

Figure 3:
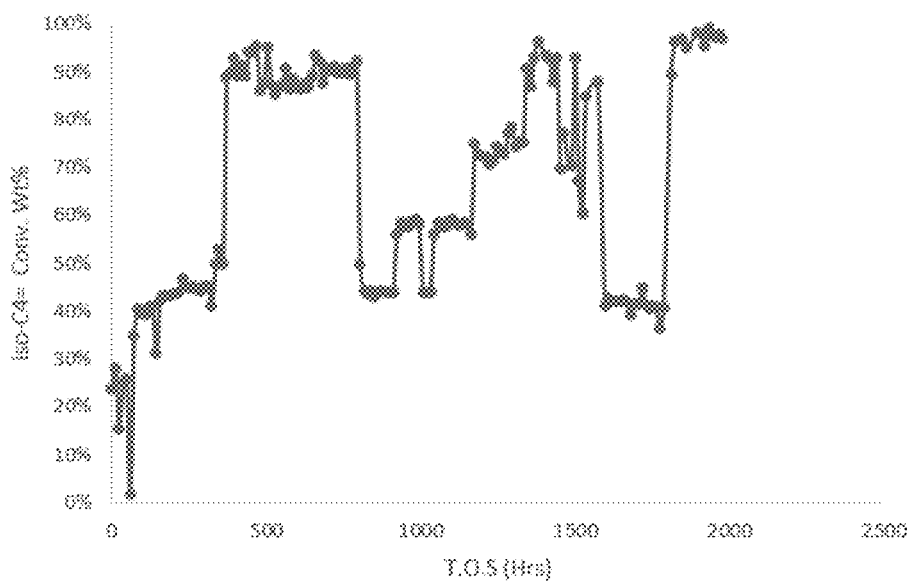
FIG. 3 depicts conversion rate of iso-butene under various conversion conditions described in Example 4.
Figure 4:
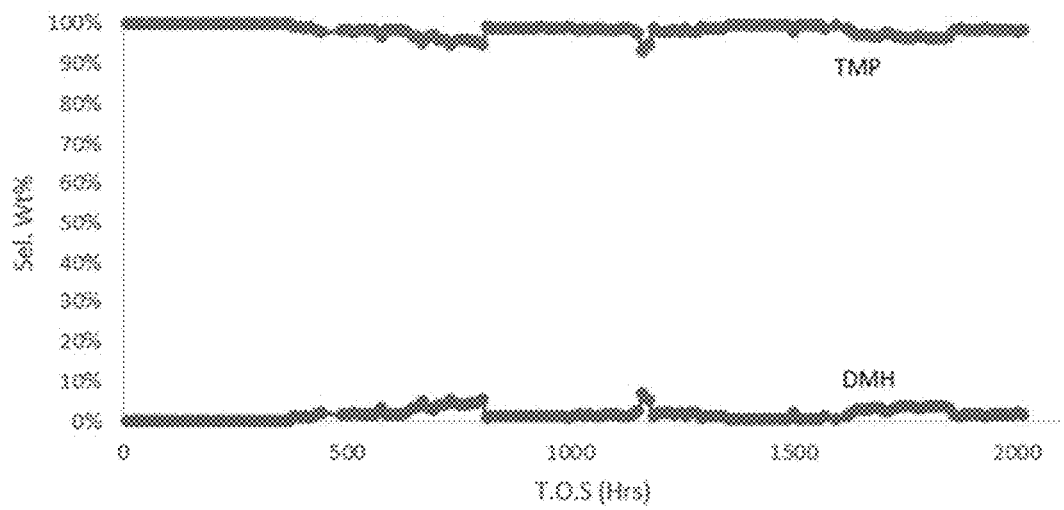
FIG. 4 depicts selectivity for trimethylpentene as compared to dimethylhexene under the conditions described in Example 4.
Figure 5:
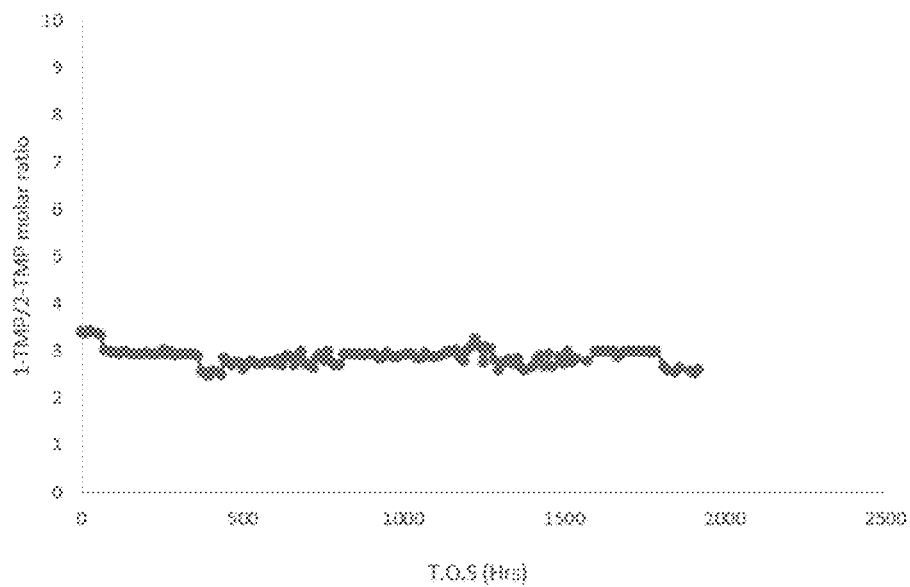
FIG. 5 depicts 2,4,4-trimethyl-1-pentene/2,4,4-trimethyl-2-pentene molar ratio under the conditions described in Example 4.

FIG. 3 shows conversion of isobutene formed from the conversion of TBA. Similarly to the conversion of TBA, the highest conversions of isobutene occur from about 400 hours to about 800 hours, from about 1200 hours to about 1600 hours, and from about 1800 hours to about 2000 hours. FIG. 4 shows the stark selectivity for trimethylpentene over dimethylhexene over the MCM-49 solid acid catalyst. Nearly 100% of the isooctene formed is trimethypentene. FIG. 5 further shows that of the trimethylpentene formed, there is a preference for 2,4,4-trimethyl-1-pentene as compared to 2,4,4-trimethyl-2-pentene by molar ratio over MCM-49.

Example 5

Dehydration/Dimerization of TBA in the Presence and Absence of Isobutane Over ZSM-48 (Comparative)

The catalyst described in Example 2 (MCM-49 of the MWW framework type) was tested in the unit with two different feeds using the procedure outlined in Example 3. The first feed was a 3:1 by volume mixture of isobutene and the TBA Blend. The second feed was the TBA Blend alone, without isobutene. The reaction was conducted with varying temperature, pressure, and space velocity (LHSV). The reaction conditions are summarized in Table 2 below.

TABLE 2

| T.O.S Hrs | feed | LHSV | Press, PSIG | Temp ° C. |
|---|---|---|---|---|
| 16-56 | 15 CC iso-butane, 5 cc blend (88% TBA, 8% acetone, 4% MeOH) | 2 | 750 | 110 |
| 64-96 | 15 CC iso-butane, 5 cc blend (88% TBA, 8% acetone, 4% MeOH) | 2 | 750 | 130 |
| 104-144 | 15 CC iso-butane, 5 cc blend (88% TBA, 8% acetone, 4% MeOH) | 2 | 750 | 150 |
| 152-216 | 15 CC iso-butane, 5 cc blend (88% TBA, 8% acetone, 4% MeOH) | 2 | 750 | 170 |
| 224-300 | 7.5 CC iso-butane, 2.5 cc blend (88% TBA, 8% acetone, 4% MeOH) | 1 | 750 | 170 |
| 308-354 | 7.5 CC iso-butane, 5 cc blend (88% TBA, 8% acetone, 4% MeOH) | 0.5 | 750 | 170 |
| 360-456 | 5 cc blend (88% TBA, 8% acetone, 4% MeOH) | 0.5 | 750 | 170 |
| 480-640 | 5 cc blend (88% TBA, 8% acetone, 4% MeOH) | 0.5 | 750 | 190 |
| 648-800 | 5 cc blend (88% TBA, 8% acetone, 4% MeOH) | 0.5 | 750 | 210 |

Figure 6:
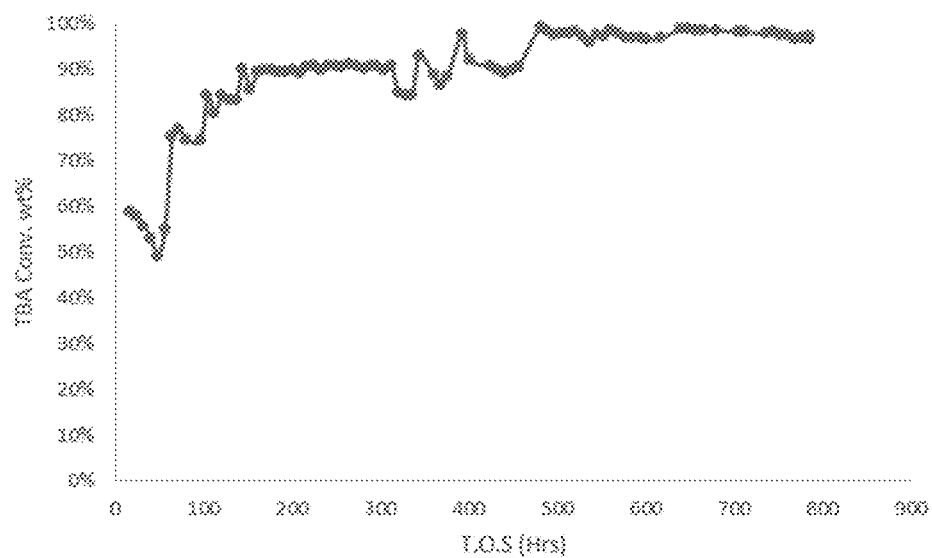
FIG. 6 depicts conversion rate of TBA under various conversion conditions described in Example 5.
Figure 7:
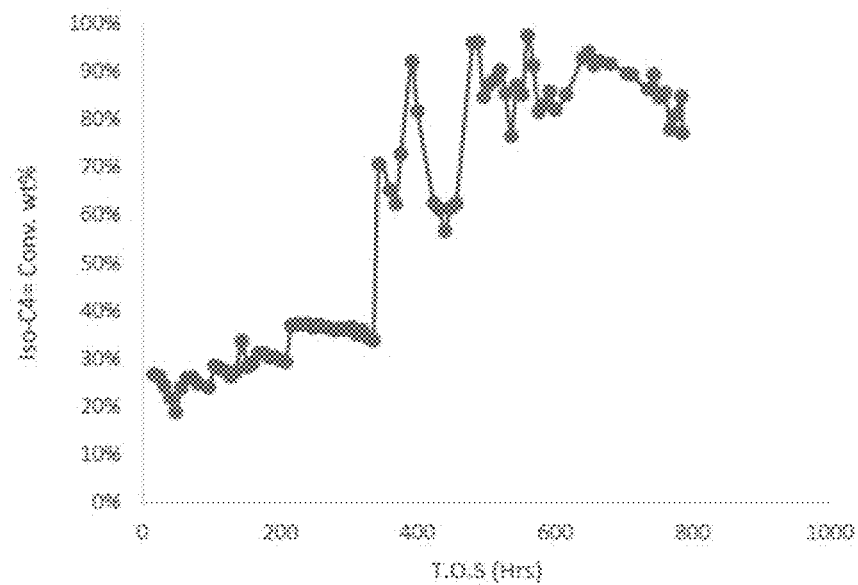
FIG. 7 depicts conversion rate of iso-butene under various conversion conditions described in Example 5.
Figure 8:
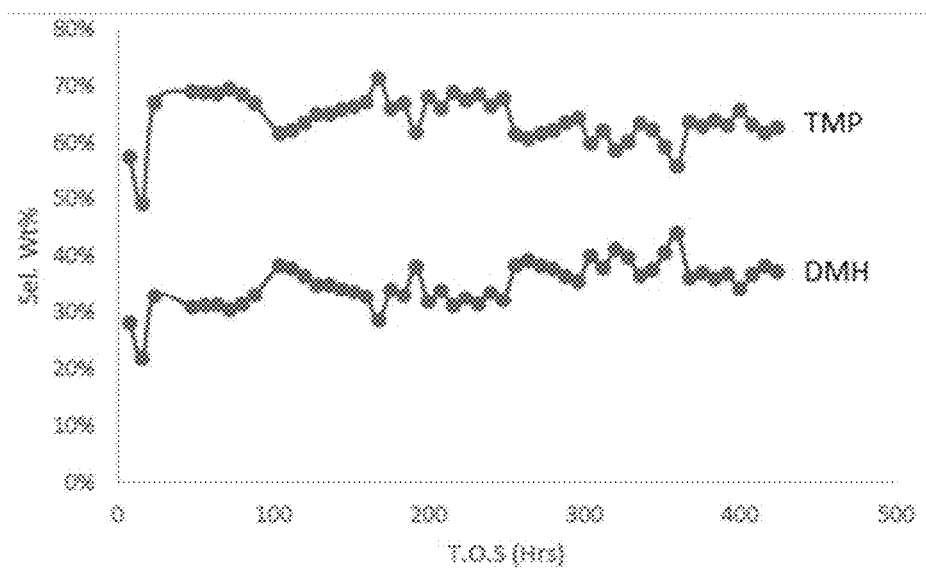
FIG. 8 depicts selectivity for trimethylpentene as compared to dimethylhexene under the conditions described in Example 5.
Figure 9:
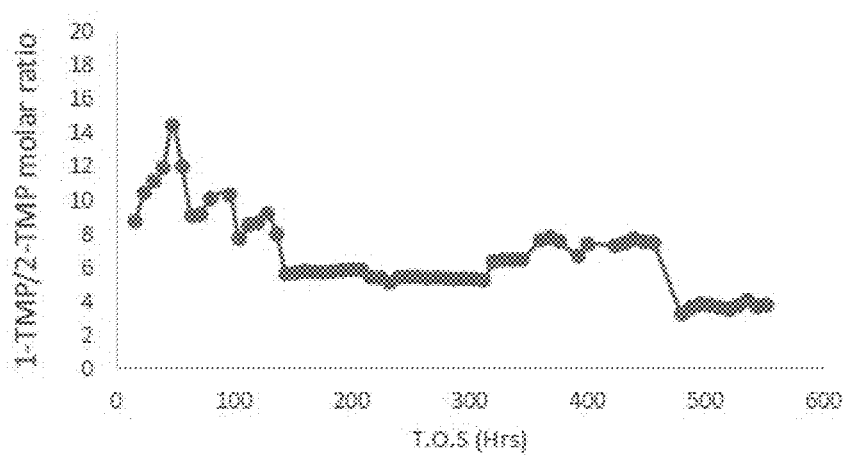
FIG. 9 depicts 2,4,4-trimethyl-1-pentene/2,4,4-trimethyl-2-pentene molar ratio under the conditions described in Example 5.

As can be seen from FIG. 6, high TBA conversion can be achieved, although not at the consistently high percentages as over MCM-49 in Example 4. The highest conversion is seen from about 150 hours to about 300 hours and from about 500 hours to about 800 hours. FIG. 7 shows conversion of isobutene formed from the conversion of TBA. Conversion of isobutene is somewhat erratic ranging from about 20-40% from 0-400 hours and from about 70-95% from 500-800 hours. FIG. 8 demonstrates a clear advantage for use of the MCM-49 catalyst over the ZSM-48 catalyst in selectivity for trimethylpentene over dimethylhexene, with the ZSM-48 catalyst having only about a 60-70% selectivity for TMP over DMH. FIG. 9 shows that of the trimethylpentene formed, there is a higher preference for 2,4,4-trimethyl-1-pentene as compared to 2,4,4-trimethyl-2-pentene by molar ratio over ZSM-48 than over MCM-49. This higher preference, however, is believed to be due to the fast isomerization of 2,4,4-trimethyl-2-pentene to dimethylhexene.

In sum, Examples 4 and 5 show that the MCM-49 catalyst (MWW framework type) exhibited excellent activity for both dehydration of TBA and dimerization of isobutene (FIGS. 2 and 3), selectivity for $C_8$ olefins (FIG. 4) in the presence of methanol and acetone, and stability (more than 1900 hours on stream). The high selectivity to trimethylpentene shown in FIG. 4 indicates that MCM-49 is resistant to isomerize trimethylpentene to dimethylhexene, which is unlike ZSM-48 (see FIG. 8). This results in a higher octane product using MCM-49. Perhaps most importantly, all of this is achieved at a reaction temperature of about 150° C. to about 190° C., with the most preferred yields occurring at a reaction temperature of about 170° C. This is achieved in the presence of impurities such as methanol and acetone.

Example 6

Procedure for Isobutene Dimerization With and Without Water Over MCM-49

For isobutene dimerization, a single reactor fixed bed isothermal pilot plant was operated without product recycle. The reactor used in these experiments comprised a stainless steel tube having an internal diameter of ⅜ inches (~0.95 cm), a length of 20.5 inches (~52 cm) and a wall thickness of 0.035 inches (~0.089 cm). A piece of stainless steel tubing 8¾ inches (~22.2 cm) long×⅜ inches (~0.95 cm) external diameter and a piece of ¼ inch (~0.64 cm) tubing of similar length were positioned in the bottom of the reactor (one inside of the other) as a spacer to position and support the catalyst in the isothermal zone of the furnace. A ¼ inch (~0.64 cm) plug of glass wool was placed at the top of the spacer to keep the catalyst in place. A ⅛ inch (~0.32 cm) stainless steel thermo-well was placed in the catalyst bed, long enough to monitor temperature throughout the catalyst bed using a movable thermocouple. The catalyst was loaded with a spacer at the bottom to keep the catalyst bed in the center of the furnace's isothermal zone.

The catalyst was then loaded into the reactor from the top. The catalyst bed contained about 4.0 g of the MCM-49 catalyst of Example 1 sized to 14-25 mesh (700 to 1400 micron) and was 10 cm in length. A ¼ inch (~0.32 cm) plug of glass wool was placed at the top of the catalyst bed to separate quartz chips from the catalyst. The remaining void space at the top of the reactor was filled with quartz chips of similar size to the catalyst or larger (such as up to 14 mesh). The reactor was installed in the furnace with the catalyst bed in the middle of the furnace at the pre-marked isothermal zone. The reactor was then pressure and leak tested at 800 psig (~5.5 MPag).

Figure 10:
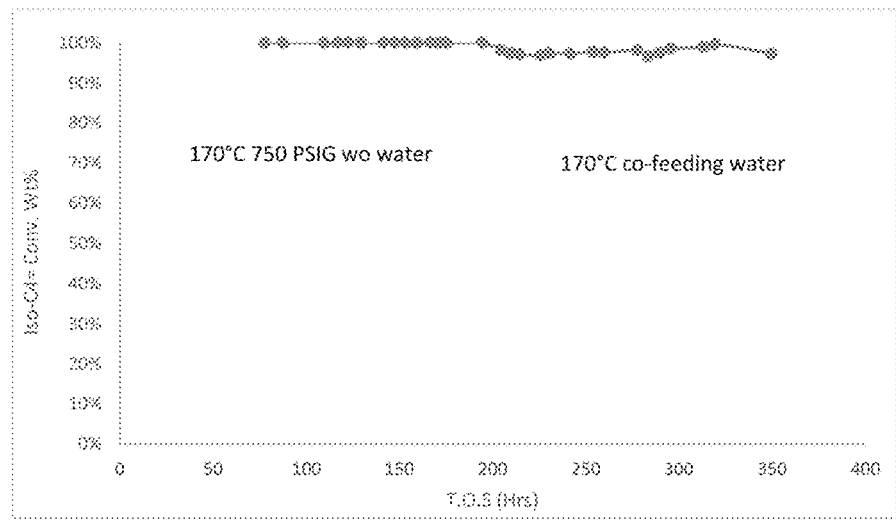
FIG. 10 depicts isobutene conversion over MCM-49 in the presence and absence of water under the conditions described in Example 6.
Figure 11:
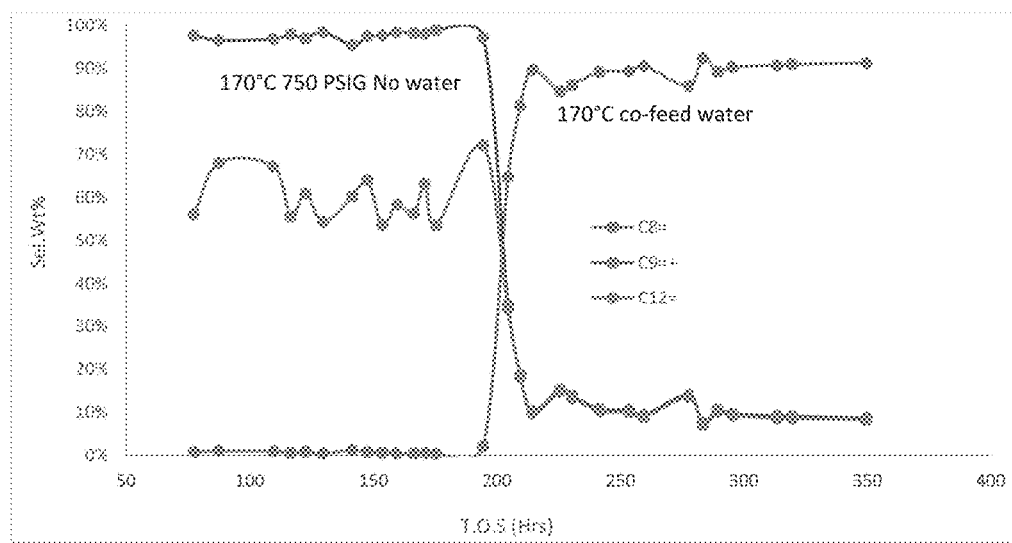
FIG. 11 depicts $C_8$ olefin selectivity over MCM-49 in the presence and absence of water under the conditions described in Example 6.

500 cc ISCO syringe pumps were used to introduce the feed to the reactor. One ISCO pump was used for pumping the water feed and a second ISCO pump was used to pump the isobutene feed. A Grove "Mity Mite" back pressure controller was used to control the reactor pressure, typically set at about 750 psig (~5.2 MPag). On-line GC analyses were taken to verify feed and the product composition. The isobutene feed (5 cc/hr) was pumped through the catalyst bed with the catalyst bed held at 170° C. for 200 hrs then the water was co-fed (0.9 cc/hr) to the reactor. The products exiting the reactor flowed through heated lines routed to GC then to cold (5-7° C.) collection pots in series. The non-condensable gas products were routed through a gas pump for analyzing the gas effluent. Material balances were taken at 24 hr intervals. Samples were taken for analysis. The material balance and the gas samples were taken at the same time while an on-line GC analysis was conducted for doing material balance. FIG. 10 shows that in the absence of water isobutene conversion was 100%, but that conversion drops slightly with the addition of water. But in FIG. 11, however, we see that the selectivity for $C_8$ olefins goes from about 0 to over 90% with co-feeding of water. Accordingly, we have shown that the presence of water, created naturally by dehydration of TBA to isobutene or added to an existing isobutene feed, produces a strong selectivity toward targeted $C_8$ olefin products. In other words, the water promotes dimerization of isobutene while at the same time hindering further polymerizations. As discussed above, it is believed that the presence of water in the feed selectively adsorbs on strong acid sites (often Bronsted acid sites) found in microporous zeolite catalysts. The adsorption of the water on the acid site decreases the acid strength of the acid site, which in turn significantly decreases the capability of the catalyst to enable further polymerizations that require these strong acid sites.

ADDITIONAL EMBODIMENTS

Embodiment 1

A method for the production of iso-octene, comprising: exposing a tert-butyl alcohol ("TBA") containing feed to a solid acid catalyst, wherein the solid acid catalyst comprises a crystalline microporous material of the MWW framework type, under dehydration conditions to convert a percentage of TBA to isobutene to form an isobutene containing feed; exposing at least a portion of the isobutene containing feed to a second solid acid catalyst, wherein the second solid acid catalyst comprises a crystalline microporous material of the MWW framework type, under dimerization conditions to dimerize isobutene molecules in the isobutene containing feed to iso-octene to form an iso-octene containing feed; wherein greater than 50% of the iso-octene molecules in the iso-octene containing feed comprise trimethylpentene relative to weight of the iso-octene feed.

Embodiment 2

The method of embodiment 1, wherein the crystalline microporous material of the MWW framework type of either the first or second solid acid catalyst is selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and mixtures thereof.

Embodiment 3

The method of any of the previous embodiments, wherein the crystalline microporous material of the MWW framework type of either the first or second solid acid catalyst is any of MCM-22, MCM-36, MCM-49 and MCM-56.

Embodiment 4

The method of any of the previous embodiments, wherein greater than 90% of the iso-octene molecules in the iso-octene containing feed comprise trimethylpentene.

Embodiment 5

The method of any of the previous embodiments, wherein greater than 95% of the iso-octene molecules in the iso-octene containing feed comprise trimethylpentene.

Embodiment 6

The method of any of the previous embodiments, wherein the trimethylpentene comprises 2,4,4,-trimethyl-1-pentene and 2,4,4,-trimethyl-2-pentene, wherein the ratio of 2,4,4,-trimethyl-1-pentene to 2,4,4,-trimethyl-2-pentene is greater than about 2.

Embodiment 7

The method of any of the previous embodiments, wherein the trimethylpentene comprises 2,4,4,-trimethyl-1-pentene and 2,4,4,-trimethyl-2-pentene, wherein the ratio of 2,4,4,-trimethyl-1-pentene to 2,4,4,-trimethyl-2-pentene is from about 2 to about 4.

Embodiment 8

The method of any of the previous embodiments, wherein the TBA containing feed is produced by oxidizing isobutane.

Embodiment 9

The method of any of the previous embodiments, wherein the dimerization conditions include a dimerization temperature of about 100° C. to about 210° C.

Embodiment 10

The method of any of the previous embodiments, wherein the dimerization conditions include a dimerization temperature of about 150° C. to about 190° C.

Embodiment 11

The method of any of the previous embodiments, wherein the dimerization conditions include a dimerization pressure of about 15 psig to about 1000 psig.

Embodiment 12

The method of any of the previous embodiments, wherein at least a portion of the TBA containing feed further comprises one or more oxygenates, the one or more oxygenates comprising water, methanol, acetone, or a combination thereof.

Embodiment 13

The method of any of the previous embodiments, wherein the TBA containing feed further comprises $C_{4+}$ isoparaffins.

Embodiment 14

The method of any of the previous embodiments, wherein the TBA containing feed further comprises acetone and methanol to form a TBA blend.

Embodiment 15

The method of any of the previous embodiments, wherein the iso-octene containing feed has an octane rating, as determined by (RON+MON)/2, of at least 95, e.g. at least 98 or at least 100.

Embodiment 16

The method of any of the previous embodiments, further comprising hydrogenating the iso-octene containing feed to form an iso-octane containing feed.

Embodiment 17

The method of any of the previous embodiments, wherein the iso-octane containing feed has an octane rating, as determined by (RON+MON)/2, of at least 100.

Embodiment 18

The method of any of the previous embodiments, wherein the solid acid catalyst comprises a mixed metal oxide based on oxides of Fe/W/Zr, W/Zr, Ce/W/Zr, Cu/W/Zr, Mn/W/Zr, or a combination thereof.

Embodiment 19

The method of any of the previous embodiments, wherein the solid acid catalyst further comprises an inorganic oxide binder.

Embodiment 20

The method of any of the previous embodiments, wherein an isobutane feed is co-fed with the TBA containing feed.

Embodiment 21

The method of embodiment 20, wherein a portion of the isobutane containing feed is oxidized to produce the TBA containing feed.

Embodiment 22

The method of any of the previous embodiments, wherein the solid acid catalyst and the second solid acid catalyst are the same.

Embodiment 23

The method of any of the previous embodiments, further comprising adding an amount of water to the TBA containing feed in addition to water formed during the conversion of TBA to isobutene.

Embodiment 24

The method of embodiment 13, further comprising removing methanol or acetone from the TBA blend and processing the removed methanol or acetone in a separate refinery application.

Embodiment 25

A method according to any of the previous embodiments, except that the oxidizing step to form TBA is omitted in favor of providing a feedstream of isobutene with added water.

The invention claimed is:

1. A method for the production of iso-octene, comprising:
exposing a tert-butyl alcohol ("TBA") containing feed, comprising one or more oxygenates, wherein the one or more oxygenates is selected from water, methanol, and acetone, to a first solid acid catalyst, wherein the first solid acid catalyst comprises a crystalline microporous material of MWW framework topology, under dehydration conditions to convert a portion of TBA to isobutene to form an isobutene containing feed; and
directly exposing at least a portion of the isobutene containing feed to a second solid acid catalyst, wherein the second solid acid catalyst comprises a crystalline microporous material of MWW framework topology, under dimerization conditions to dimerize isobutene molecules in the isobutene containing feed to iso-octene to form an iso-octene containing feed, wherein greater than 50% of iso-octene molecules in the iso-octene containing feed comprise trimethylpentene.

2. The method of claim 1, wherein the crystalline microporous material of MWW framework topology of either the first or second solid acid catalyst is selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and mixtures thereof.

3. The method of claim 1, wherein the crystalline microporous material of MWW framework topology of either the first or second solid acid catalyst is any of MCM-22, MCM-36, MCM-49 and MCM-56.

4. The method of claim 3, wherein greater than 90% of the iso-octene molecules in the iso-octene containing feed comprise trimethylpentene.

5. The method of claim 3, wherein greater than 95% of the iso-octene molecules in the iso-octene containing feed comprise trimethylpentene.

6. The method of claim 3, wherein the trimethylpentene comprises 2,4,4,-trimethyl-1-pentene and 2,4,4,-trimethyl-2-pentene, wherein the ratio of 2,4,4,-trimethyl-1-pentene to 2,4,4,-trimethyl-2-pentene is greater than about 2.

7. The method of claim 3, wherein the trimethylpentene comprises 2,4,4,-trimethyl-1-pentene and 2,4,4,-trimethyl-2-pentene, wherein the ratio of 2,4,4,-trimethyl-1-pentene to 2,4,4,-trimethyl-2-pentene is from about 2 to about 4.

8. The method of claim 1, wherein the TBA containing feed is produced by oxidizing isobutane.

9. The method of claim 1, wherein the dimerization conditions include a dimerization temperature of about 100° C. to about 210° C.

10. The method of claim 1, wherein the dimerization conditions include a dimerization temperature of about 150° C. to about 190° C.

11. The method of claim 1, wherein the dimerization conditions include a dimerization pressure of about 15 psig to about 1000 psig.

12. The method of claim 1, wherein the TBA containing feed further comprises $C_{4+}$ isoparaffins.

13. The method of claim 12, wherein the TBA containing feed further comprises acetone and methanol to form a TBA blend.

14. The method of claim 1, wherein the iso-octene containing feed has an octane rating, as determined by (RON+MON)/2, of at least 95.

15. The method of claim 1, further comprising hydrogenating the iso-octene containing feed to form an iso-octane containing feed.

16. The method of claim 1, wherein the iso-octene containing feed has an octane rating, as determined by (RON+MON)/2, of at least 100.

17. The method of claim 1, wherein the first solid acid catalyst comprises a mixed metal oxide based on oxides of Fe/W/Zr, W/Zr, Ce/W/Zr, Cu/W/Zr, Mn/W/Zr, or a combination thereof.

18. The method of claim 1, wherein the first solid acid catalyst further comprises an inorganic oxide binder.

19. The method of claim 1, wherein an isobutane feed is co-fed with the TBA containing feed.

20. The method of claim 19, wherein a portion of the isobutane feed is oxidized to produce the TBA containing feed.

21. The method of claim 1, wherein the first solid acid catalyst and the second solid acid catalyst are the same.

22. The method of claim 1, further comprising adding an amount of water to the TBA containing feed in addition to water formed during the conversion of TBA to isobutene.

23. The method of claim 13, further comprising removing methanol or acetone from the TBA blend and processing the removed methanol or acetone in a separate refinery application.

* * * * *